United States Patent [19]

Fenton, Jr. et al.

[11] Patent Number: 4,673,394
[45] Date of Patent: Jun. 16, 1987

[54] IMPLANTABLE TREATMENT RESERVOIR

[75] Inventors: Paul V. Fenton, Jr., Marblehead; Thomas M. Young, North Andover, both of Mass.

[73] Assignee: Strato Medical Corporation, Beverly, Mass.

[21] Appl. No.: 820,714

[22] Filed: Jan. 17, 1986

[51] Int. Cl.$^4$ ............................................. A61M 5/00
[52] U.S. Cl. .................... 604/175; 604/236; 604/905; 128/912
[58] Field of Search ............... 604/175, 51, 52, 236, 604/237, 905; 128/912

[56] References Cited

U.S. PATENT DOCUMENTS

| | | |
|---|---|---|
| 3,310,051 | 3/1967 | Schulte . |
| 3,783,876 | 1/1974 | Dye ..................................... 604/117 |
| 3,990,445 | 11/1976 | Lundquist . |
| 4,014,328 | 3/1977 | Cluff et al. . |
| 4,108,174 | 8/1978 | Slivenko ............................. 604/175 |
| 4,190,040 | 2/1980 | Schulte . |
| 4,304,228 | 12/1981 | Depel .................................. 128/912 |
| 4,400,169 | 8/1983 | Stephen . |
| 4,405,305 | 9/1983 | Stephen et al. . |
| 4,445,896 | 5/1984 | Gianturco . |
| 4,490,137 | 12/1984 | Moukheibir ........................ 604/175 |
| 4,543,088 | 9/1985 | Bootman et al. . |
| 4,569,675 | 2/1986 | Prosl et al. ......................... 604/175 |
| 4,581,020 | 4/1986 | Mittleman .......................... 604/175 |
| 4,583,977 | 4/1986 | Shishov et al. ..................... 604/175 |

FOREIGN PATENT DOCUMENTS 0134745 3/1985 European Pat. Off. ............ 604/175

Primary Examiner—C. Fred Rosenbaum
Assistant Examiner—John D. Ferros
Attorney, Agent, or Firm—Lahive & Cockfield

[57] ABSTRACT

An implantable treatment device has a housing portion defining a chamber and a self-resealable cover portion which closes off the chamber to provide a fluid receiving reservoir. An exit port extends from the reservoir to the external surface of the housing, and a locking member affixed to the device permits a twist-lockable catheter connection to be securely sealed to the exit port. In one embodiment the locking member is a base plate having a slot therein to capture the flange of a catheter connection. A protruding tab on the catheter connection may be sutured to hold the twist-locked connection in a fixed orientation. A multi-reservoir and multi-catheter embodiment is shown. A preferred implantable multi-reservoir device includes tactile features palpable through the skin for distinguishing the different reservoirs, or identifying the contents thereof.

12 Claims, 10 Drawing Figures

IMPLANTABLE TREATMENT RESERVOIR

TECHNICAL FIELD

This invention relates to implantable treatment material reservoirs for providing a treatment material, such as a drug in fluid form, directly to the vascular system of a mammal. A number of such devices are known, and may be broadly described as having a housing which defines a reservoir for holding the treatment material, and a catheter leading from the housing for interconnecting the reservoir with the vascular system. Existing implantable devices are adapted to be sutured into place within the body.

The existing devices known to the inventor are of two types. The first type has a catheter permanently affixed to the reservoir housing. Such permanent affixation makes the device awkward to implant. The second type has a catheter which fits over a male tube projecting from the housing, and is secured thereto by placing an external collar about the catheter. This device permits the housing to be sutured in position, and the catheter to be installed in a vein and sized before connection of the catheter to the housing. However, the connection of the catheter requires care and it relies solely on elastic gripping to remain attached. It is desirable to provide an implantable reservoir device which permits the direct and simple yet secure connection to a catheter after the suturing of the reservoir housing in the body and the placement and sizing of the catheter.

OBJECTS AND SUMMARY OF THE INVENTION

It is an object of the invention to provide an implantable reservoir for the delivery of the treatment materials to the vascular system of a mammal.

It is another object of the invention to provide such a reservoir of which may be refilled from outside the body.

It is another object of the invention to provide an implantable reservoir device adapted to provide plural separate treatment materials to the vascular system.

It is another object of the invention to provide an implantable reservoir adapted to be securely affixed in a desired position.

It is another object of the invention to provide an implantable reservoir having a simple yet secure means of connection to the vascular system.

It is another object of the invention to provide an implantable reservoir which permits simple attachment of a catheter to the reservoir after sizing of the catheter and after placement of the catheter and surgical attachment of the reservoir to the body, yet provides assured integrity of the catheter connection.

These and other desirable features are achieved according to the invention in an implantable device in which a housing has an interior reservoir with an exit port defining a flow path from the reservoir. A mounting means formed on the housing at the exit port is adapted to engage a mating twist lockable catheter connector. This permits the device to be surgically placed in the body, and the catheter to be connected to a vein, prior to connection of the device with the catheter, allowing greater maneuverability and better fitting during the surgical installation. In a preferred embodiment, the housing portion defines a fluid receiving chamber, and a cover portion made of self-resealing polymer closes off the chamber to provide the reservoir for holding treatment material. The reservoir may be refilled from outside the body using a hypodermic syringe to inject treatment fluid through the cover portion. The housing has a base plate with an opening adjacent to the exit port. The catheter connector fits around the catheter and has a radially extending flange, shaped so that when the connector is rotated the opening captures the flange to lock the catheter in position. In a further preferred embodiment, the mating twist-lockable connector of the catheter has a protruding tab oriented, when twist-locked to the mounting means, to be sutured against the base plate to prevent rotation of the connector. Multi-chamber devices and a preferred catheter connector are shown. In a preferred multi-chamber device, tactile features are palpable through the skin to distinguish the different chambers.

BRIEF DESCRIPTION OF THE DRAWINGS

These and other features of the invention will be understood with reference to the figures, in which.

DETAILED DESCRIPTION

Figure 1:
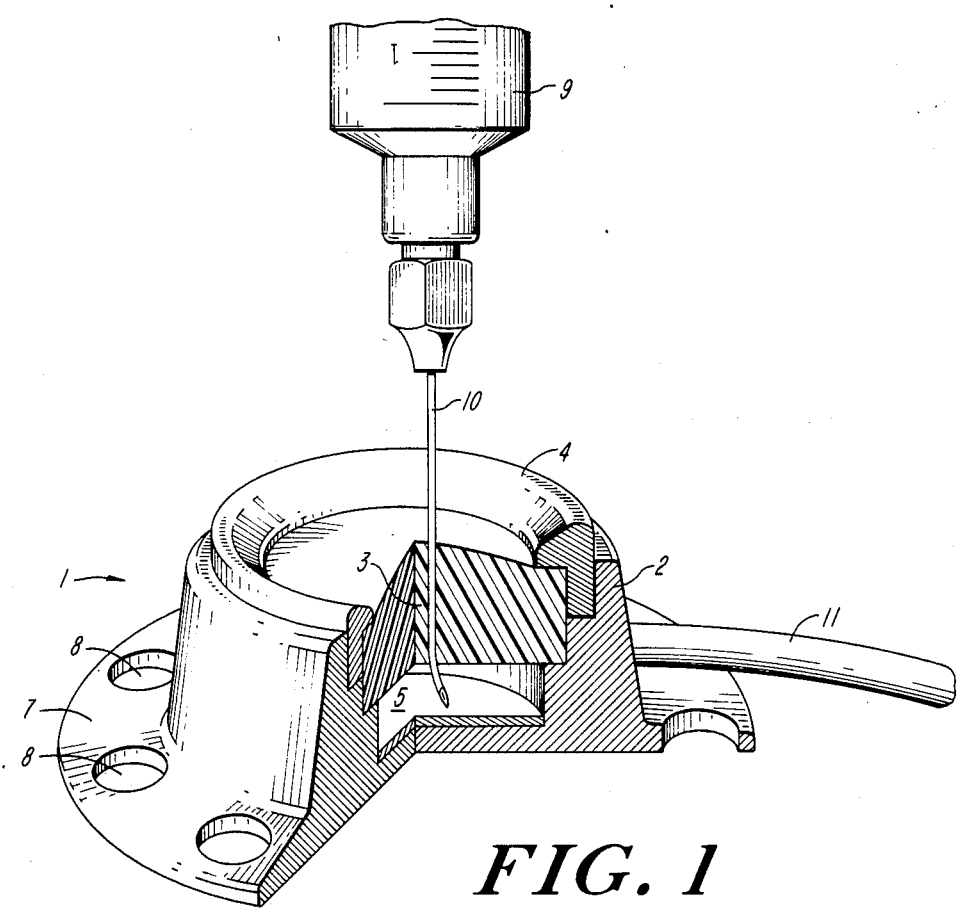
FIG. 1 shows a cut-away pictorial view of an implantable device according to the invention.

FIG. 1 shows a cutaway pictorial view of an implantable device 1 according to the present invention. Device 1 includes a housing 2 defining a generally cup-shaped recess forming a reservoir cavity 5 for holding treatment fluids or medicine. Housing 2 has an open face which is closed off by a cover member 3 held down by a retaining ring 4. Cover member 3 is formed of a self-resealing polymer, which is preferably an elastomer such as a silicone rubber or latex, and is adapted to permit access using a hypodermic needle to the reservoir cavity 5 formed by the cover 3 and the housing 2. Housing 2 is formed of a biocompatible material, such as electropolished 316L stainless steel, or other surgical grade steel or biocompatible hard material. At the base of the reservoir 5 a protection plate 6 formed of a suitable material, such as a high durometer silicone rubber, is placed to prevent damage to a needle tip. Housing 2 has a generally cup-shaped form, rising from a base plate 7. Plate 7 has apertures therein evenly spaced about the perimeter of the housing for suturing the device to a layer of tissue when implanting. Also shown in FIG. 1 is a syringe 9 having a non-coring needle 10. Syringe 9 is shown by way of illustration having penetrated the septum or cover 3, in position to refill the reservoir. A catheter 11 leads from the reservoir to the vascular system of the subject.

Figure 2:
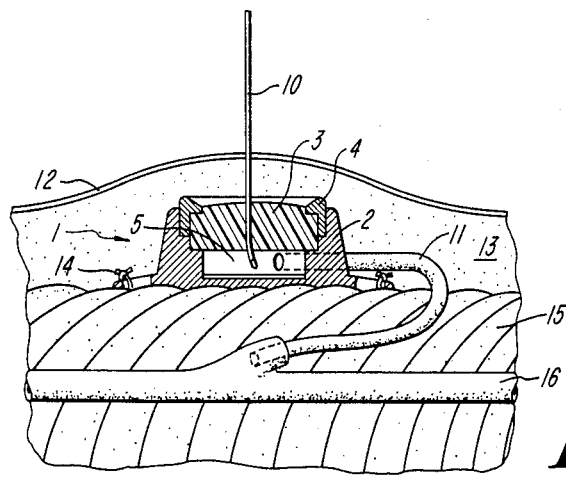
FIG. 2 shows a schematic section of the device of FIG. 1 implanted beneath the skin of a mammal.

FIG. 2 shows a schematic section of the device 1 implanted beneath the skin of a mammal. As shown, device 1 lies beneath the skin 12 in the sub-cutaneous tissue 13 of the mammal. One or more sutures 14 through apertures 8 of the baseplate attach device 1 to the muscle fascia 15, and catheter 11 leads from the housing to the vascular system 16 of the mammal. The housing 2 of device 1 has a low profile and a broad flat base. This geometry orients the septum 3 to face outwardly toward the skin, so that the reservoir may be repeatedly and conveniently refilled. Needle 10 is shown in position to refill the reservoir.

It will be appreciated that because device 1 is sutured directly to the mammal, a high degree of maneuverability of the device or accessibility of the suture apertures 8 is desired for the surgical process of implantation. However, because device 1 connects directly via catheter 11 to the vascular system, the integrity of the catheter connection must also be assured. Furthermore, it is desirable to size the length of the catheter after one end has been placed into a vein and the catheter threaded into position. According to the present invention these ends are achieved by providing in the housing a low profile mounting means adapted to receive a separate twist-lockable catheter connection which fits over the sized catheter. Safety means secures the twist-locked catheter to the housing in fixed orientation.

Figure 3A:
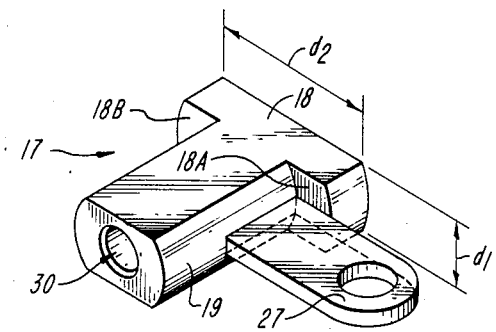
FIG. 3A shows a perspective of a preferred female catheter connector.
Figure 3B:
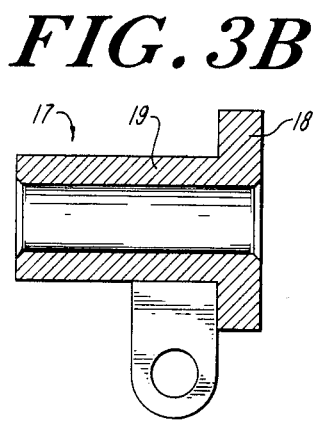
FIG. 3B shows a plane section through the preferred connection of FIG. 3A.
Figure 4A:
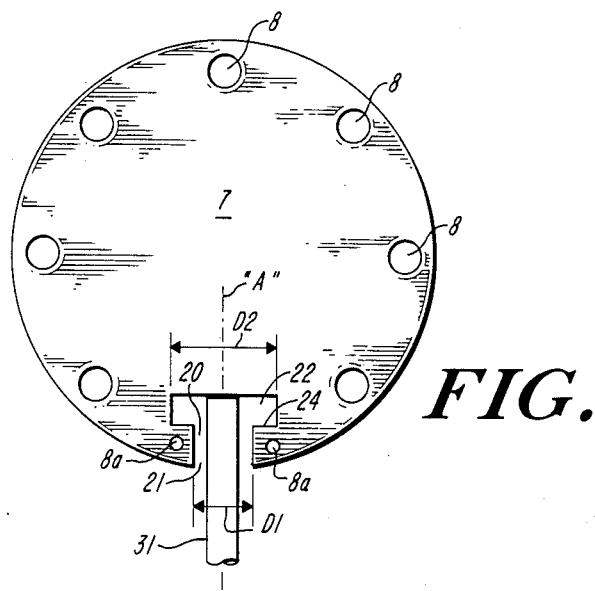
FIG. 4A shows a bottom view of the device of FIG. 1 having a mount formed on the housing for accomodating the catheter connector of FIGS. 3A, 3B.
Figure 4B:
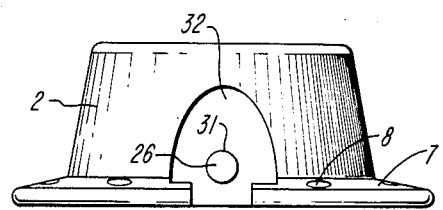
FIG. 4B shows the side view seen from the catheter flow axis of the device shown in FIG. 4A.
Figure 4C:
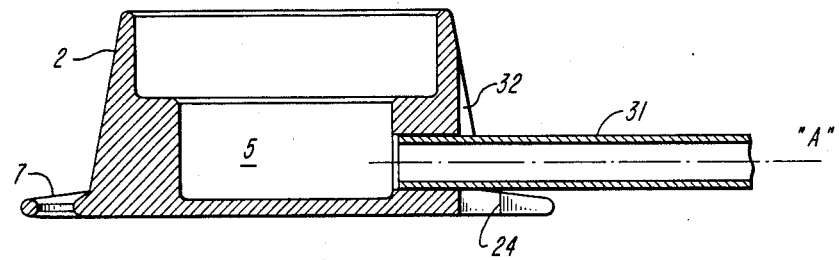
FIG. 4C shows a vertical section of the device of FIGS. 4A, 4B, in a plane containing the flow axis.

FIGS. 3A, 3B show views of a catheter end twist-lock connector. FIGS. 4A, 4B and 4C show a corresponding mating mounting structure on the housing 2 of device 1, adapted to receive the catheter shown in FIGS. 3A, 3B in accordance with the invention.

FIG. 3A is a perspective from the catheter end of a catheter connector 17. Connector 17 comprises a peripheral flange portion 18 and a central portion 19 having a bore 30 there through for fitting over a catheter in such a manner as to be slideably moved therealong. Flange 18 comprises opposed arcuate flange segments 18A, 18B extending radially outward from central portion 19. Flange 18 has a minimum cross-dimension $d_1$ in a first direction and a maximum cross-dimension $d_2$ in a second direction angularly offset therefrom. Connector 17 also includes a tab 27, discussed further below in relation to FIG. 5.

FIG. 3B shows a section through the connector of FIG. 3A. As shown, flange portion 18 extends in a direction radially outward from the central flow axis of the catheter. Inwardly thereof, portion 19 defines a generally tubular body oriented along the catheter flow axis. Body 19 serves as a collar, and has an inner diameter calculated to elastically compress the catheter when the catheter has been slipped over an inner cannula to attach it to the reservoir.

FIG. 4A shows a bottom view of housing 2 of the device 1 for receiving a catheter 11 and connector 17. As shown, the housing comprises a substantially disc-shaped base member 7 having apertures 8 evenly spaced about the perimeter thereof. A vertical T slot 20 is formed in base 7 with the axis "A" of the T oriented along the radius of the disc. Slot 20 comprises an axial portion 21 and an inner or cross portion 22. As shown, axial portion 21 is aligned with the radius of the base member, and cross portion 22 is perpendicular thereto. The width $D_1$ of axial portion 21 is slightly greater then the width $d_1$ in the narrow direction of flange portion 18 of the catheter connector (FIG. 3A) to which it is matched, and less than $d_2$. Thus the catheter connector may be slideably fitted into the T slot along axis A. Cross portion 22 has a width greater than slot 21, allowing rotation of the connector. Thus, when the catheter connector 17 is moved axially into opening 21 and butted up against the housing 2, rotation of the catheter connector within cross slot 22 results in positioning the flange 18 behind an inner surface 24 of cross portion 22. Portion 24 thus traps the catheter connector 17 within the T-slot 20 in the manner of a bayonet mount to prevent axial motion thereof. FIG. 4A also shows cannule 31, which is press fit into the housing 2 so as to provide a fluid outlet from the reservoir. Cannule 19 in a prototype embodiment is a straight tube, having a diameter small enough so that the catheter may be slideably fitted thereover, yet large enough to firmly compress the catheter when the connector 17 is placed over the catheter.

FIG. 4B shows a side view along the central axis A of the T slot 20 and housing 2. Housing 2 has an aperture 26 formed along the axis A of slot 20, and communicating directly to the reservoir (5 of FIG. 1) located therein. Cannula 31 is fitted by an interference fit in aperture 26 for receiving the catheter prior to sliding the connector 17 along T-slot 20. A rotation of the catheter connector 17 then engages its flange 18 behind an extending arm of which a surface (24 of FIG. 4A) thereby engages the catheter connector firmly to prevent its pulling away from the housing. This establishes secure fluid communication between the reservoir and the catheter.

FIG. 4C shows a vertical section along the outflow axis "A" of the device 1. A face 32 of housing 2 lying perpendicular to axis A is preferably milled flat when forming the T-slot. The central recess of the housing is a stepped bore, which defines the reservoir portion 5 and a circular recess for holding the elastomeric cover portion (not shown). A tube or cannula 31 extends from the reservoir to receive a catheter.

Figure 5:
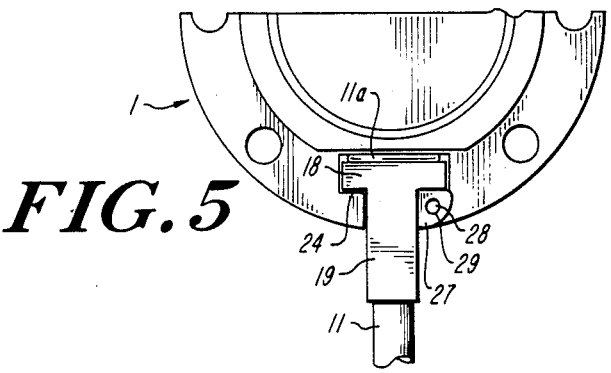
FIG. 5 shows a top view of the device and catheter of FIGS. 1 through 4 with the catheter secured in its twist-locked position.

FIG. 5 shows a top view of device 1 with the preferred twist-lock catheter mounted in position. As shown, the catheter has been inserted in T slot 20 and rotated so as to bring flange 18 into engagement behind inner face 24 of the cross portion of the T. In this position, tab 27 protruding from connector 17 is brought down flush against the base plate 7. Tab 27 is shown held by a structure which provides positive resistance to counter-rotation of the catheter which might lead to its detachment. The tab 27 lies in a plane oriented, with respect to the flange 18 of the connector 17 so as to assure that, when held in position against base 7, flange 18 is held fully rotated in slot 20, whereby the connector is positively locked in the housing. In the preferred embodiment tab 27 has an aperture 28 therethrough, and may be sutured down against the base plate with sutures 29. The sutures 29 pass through corresponding holes in the base member, shown as holes 8a in FIG. 4A. Catheter 11 is compressed between the inner face of collar 19 of the connector, and the cannula 31 (FIGS. 4A-4C). In addition, when the connector is installed, the catheter "bunches up" at 11a into a thickened donut-shaped mass which provides an axially directed elastic force along axis A. The resultant pressure between flange 18 and face 24 further inhibits rotation of connector 17.

Figure 6:
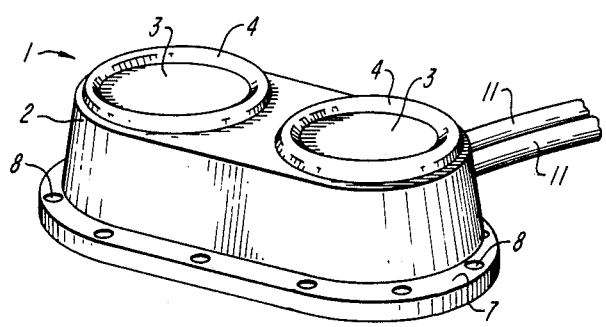
FIG. 6 shows a perspective view of a multiple reservoir device according to the invention.

FIG. 6 shows a perspective view of an implantable device having two reservoirs, with the numbered elements corresponding to the identically numbered parts of FIGS. 1 through 5.

Figure 6A:
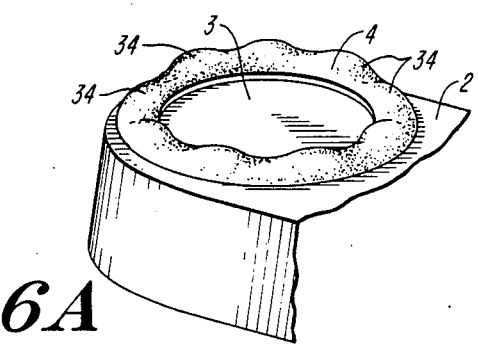
FIG. 6A shows a detail of a preferred embodiment of a multiple reservoir device.

FIG. 6A shows a detail of a preferred embodiment of a multi-reservoir implantable device, such as the device of FIG. 6, but having formed thereon bumps or other tactile features which may be felt through the skin when implanted, to identify a reservoir thereof. Retaining ring 4 has a scalloped upper surface with such bumps 34 thereon, so that the bumps 34 outline the septum 3 in a manner easily felt from outside the body. Thus the bumps indicate the location of a reservoir or injection site. In the event it is desired to have more than two reservoirs, which may be placed in a cloverleaf or other cluster configuration, the tactile features preferably include different arrangements of tactile features which additionally each serve as a "code" for the particular medicine which is to be held by that reservoir.

It will be appreciated that other forms of twist-lock coupling of a catheter to the housing are possible, and that for a given catheter bayonet structure, the corresponding mounting structure on the housing may be fabricated. According to the principle of one aspect of the invention, the housing includes an exit port from its reservoir and a mounting means on the exit port adapted to receive a mating twist-lock catheter connection. Thus, details of the housing mounting will vary according to the selected bayonet coupling. It will be further appreciated that while this aspect of the invention has been described in respect to a preferred embodiment having a single treatment material reservoir, the invention includes such implantable devices having plural fluid reservoirs, and various housing structures. Furthermore the tactile features for distinguishing may take various forms, from a single bump to a coded pattern, and may be placed upon the septum itself, the housing or other palpable portion of the device.

The invention having been thus disclosed and described, variations and modifications will occur to those skilled in the art and all such variations are intended to be included within the scope of the invention, as defined by the following claims.

What is claimed is:

1. A vascular access port for surgical implantation in the body of a mammal, such access port comprising:
   a body portion formed of biocompatible material and defining a chamber with an open face,
   cover means for closing the chamber thereby forming a closed reservoir for receiving treatment material, said cover means being formed of a self-resealing penetrable polymer,
   said body portion having formed therein an access aperture communicating with the closed reservoir, and also having lock means formed adjacent to the aperture for releasably engaging a flange of a mating twist-lockable connection, said lock means including a region of the bounding surface of said body portion, said region defining a void region adjacent to said aperture exterior to said reservoir and including means for releasably engaging said flange by a partial revolution of such connection, whereby the reservoir may be placed in fluid communication with a catheter having such a mating twist-lockable connection.

2. An access port according to claim 1, wherein the body portion defines plural chambers, each with an open face, and wherein the cover means closes each chamber, thereby defining plural closed reservoirs, the body portion including an access aperture and a corresponding lock means for each said reservoir.

3. A vascular access port according to claim 1 or 2, wherein the lock means includes a means for guiding a catheter connector for rotational motion about an axis passing through the aperture and means for capturing the connector so as to prevent motion of the connector along the axis when rotated.

4. A vascular access port according to claim 3, wherein the body portion includes base portion adapted for suturing to the body tissue of the mammal.

5. A vascular access port according to claim 4, wherein the body portion includes means for securing the connection against rotational motion.

6. An implantable assembly comprising:
   A. an implantable device with an interior reservoir and exit port coupled thereto, said exit port defining a flow path from said reservoir along an exit axis,
   B. a catheter having a central passage and an entry port coupled thereto, said entry port defining a flow path to said central passage along a central axis,
   C. a coupling means for detachably coupling said exit port and said input port and selectively establishing a continuous flow path between said reservoir and said central passage with said exit axis and said central axis being coaxial, wherein said coupling means includes:
      i. twist-lockable connector surrounding said entry port of said catheter, said connector extending along said central axis and including a flanged portion adjacent to a base portion, said flanged portion including a flange extending radially outwardly with respect to said central axis, said flanged portion having a maximum dimension $d_1$ in a first direction and a maximum dimension $d_2$ in a second direction rotationally offset from said first direction about the central axis, and said base portion having dimensions essentially no larger than $d_1$ in said first and second directions, said central axis being perpendicular to said first direction and said second direction,
      ii. a locking member affixed to said device, said member including a locking portion defining an opening extending along said exit axis, and adapted to receive said flanged portion of said connector, said opening having an input region large enough to permit passage of said flange portion therethrough and an interior region large enough to receive therein said flange portion at all angular orientations about said exit axis with said central and exit axes coaxial, said input region having a maximum dimension $D_1$ in a third direction perpendicular to said central axis, where $D_1$ is less than $d_2$.

7. A vascular access device implantable in the body of a mammal having a housing portion defining plural distinct reservoirs for receiving treatment fluids, at least one of said reservoirs having an exit port, and a self-resealing cover portion for sealing said reservoir while permitting access thereto for refilling by hypodermic injection through said cover portion from outside the body, wherein the device further includes tactile means, palpable from outside the body and including at least two distinct patterned regions, each of said regions being located proximal to a respective one of said reservoirs, for distinguishing between said plural distinct reservoirs.

8. An implantable device according to claim 7, wherein each said patterned region of the tactile means defines an outline, palpable through the skin, of the self-resealing cover portion of one of said reservoirs.

9. An implantable device according to claim 7 or 8 wherein at least one of said patterned regions represents a particular drug to be injected into one of said reservoirs.

10. A vascular access port for surgical implantation in the body of a mammal, such access port comprising:
a body portion formed of biocompatible material and defining a chamber with an open face,
cover means for closing the chamber thereby forming a closed reservoir for receiving treatment material, said cover means being formed of a self-resealing penetrable polymer,
said body portion having formed therein an access aperture communicating with said closed reservoir, and said body portion including a bounding surface region defining a void region adjacent to the aperture, and exterior to said reservoir, said bounding surface region including means for releasably engaging a flange of a mating twist-lockable hollow bore connector, whereby upon partial resolution of said connector so that said flange engages said engaging means the reservoir is in fluid communication with the interior of said hollow bore connector.

11. An access port according to claim 10, wherein the body portion defines plural chambers, each with an open face, and wherein the cover means closes each chamber, thereby defining plural closed reservoirs, the body portion including an access aperture and a corresponding void region for each said reservoir.

12. A vascular access port according to claim 10 further including guide means for guiding a flange-bearing hollow bore connector for rotational motion about an axis passing through said access aperture so as to guide the flange of said connector into engagement with said engaging means, thereby capturing the connector so as to prevent motion of the connector along said axis when said flange is so engaged.

* * * * *